United States Patent
Barnes et al.

(10) Patent No.: US 10,022,544 B2
(45) Date of Patent: Jul. 17, 2018

(54) VISION ENHANCEMENT APPARATUS FOR A VISION IMPAIRED USER

(71) Applicant: NATIONAL ICT AUSTRALIA LIMITED, Eveleigh, NSW (AU)

(72) Inventors: Nick Barnes, Eveleigh (AU); Xuming He, Eveleigh (AU)

(73) Assignee: NATIONAL ICT AUSTRALIA LIMITED, Eveleigh, New South Wales (AU)

( * ) Notice: Subject to any disclaimer, the term of this patent is extended or adjusted under 35 U.S.C. 154(b) by 181 days.

(21) Appl. No.: 14/904,829

(22) PCT Filed: Jul. 22, 2014

(86) PCT No.: PCT/AU2014/050142
§ 371 (c)(1),
(2) Date: Jan. 13, 2016

(87) PCT Pub. No.: WO2015/010164
PCT Pub. Date: Jan. 29, 2015

(65) Prior Publication Data
US 2016/0199649 A1     Jul. 14, 2016

(30) Foreign Application Priority Data
Jul. 22, 2013 (AU) ............................. 2013902718

(51) Int. Cl.
*G06K 9/00* (2006.01)
*A61N 1/36* (2006.01)
(Continued)

(52) U.S. Cl.
CPC .......... *A61N 1/36046* (2013.01); *G06T 5/008* (2013.01); *G06T 5/50* (2013.01);
(Continued)

(58) Field of Classification Search
None
See application file for complete search history.

(56) References Cited

U.S. PATENT DOCUMENTS

2002/0010496 A1   1/2002 Greenberg et al.
2005/0179784 A1   8/2005 Qi
(Continued)

FOREIGN PATENT DOCUMENTS

WO   WO 2009/126258   10/2009
WO   WO 2011/038465    4/2011
WO   WO 02/089043     11/2011

OTHER PUBLICATIONS

PCT International Search Report and the Written Opinion of the International Searching Authority, Australian Patent Office, PCT/AU2014/050142, 9 pages, dated Aug. 15, 2014.
(Continued)

*Primary Examiner* — Tahmina Ansari

(57) ABSTRACT

This disclosure concerns a method for enhancing vision for a vision impaired user comprises. A processor, such as a controller of a retinal prosthesis, determines based on input image data a shape associated with an object represented by the input image data. The processor then determines for each of multiple areas of the input image data a coverage value that indicates to what extent the shape covers that area of the input image. Each of the multiple areas is associated with one of multiple imaging elements of the retinal prosthesis. The processor then determines an output value for each of the multiple imaging elements of the retinal prosthesis, such that when the output values are applied to the imaging elements to create a visual stimulus, a contrast is perceivable between a first element and a second element based on their respective coverage values.

19 Claims, 5 Drawing Sheets

(51) Int. Cl.
  G06T 5/00    (2006.01)
  G06T 5/50    (2006.01)
  G06T 7/11    (2017.01)
  G06T 7/162   (2017.01)
  G06T 7/174   (2017.01)

(52) U.S. Cl.
  CPC .............. *G06T 7/11* (2017.01); *G06T 7/162* (2017.01); *G06T 7/174* (2017.01); *G06T 2207/10016* (2013.01); *G06T 2207/10024* (2013.01); *G06T 2207/20072* (2013.01); *G06T 2207/30041* (2013.01)

(56) References Cited

U.S. PATENT DOCUMENTS

| | | | |
|---|---|---|---|
| 2008/0046029 A1 | 2/2008 | McClure et al. | |
| 2009/0256918 A1 | 10/2009 | Rabinowitz et al. | |
| 2011/0085049 A1 | 4/2011 | Dolgin et al. | |
| 2012/0242801 A1* | 9/2012 | Barnes ............... | A61N 1/36046 348/46 |
| 2016/0199649 A1* | 7/2016 | Barnes ............... | A61N 1/36046 382/128 |

OTHER PUBLICATIONS

C. McCarthy et al., "Ground surface segmentation for navigation with a low resolution visual prosthesis", 2011 Annual International Conference of the IEEE Engineering in Medicine and Biology Society EMBC, Aug. 30, 2011, pp. 4457-4460.

J. Dowling et al., "Intelligent Image Processing Constraints for Blind Mobility Facilitated through Artificial Vision", Proceedings of the 8th Australian and New Zealand Intelligent Information Systems Conference, 2003, pp. 109-114.

C. McCarthy et al., "Augmenting Intensity to Enhance Scene Structure in Prosthetic Vision", 2013 IEEE International Conference on Multimedia and Expo Workshops, Jul. 15, 2013, pp. 1-6.

M. Pawan Kumar et al., "OBJCUT: Efficient Segmentation Using Top-Down and Bottom-Up Cues", IEEE Transactions on Pattern Analysis and Machine Intelligence, vol. 32, No. 3, Mar. 2010, pp. 530-545.

M. Grundmann et al., "Efficient Hierarchical Graph-Based Video Segmentation", 2010 IEEE Conference on Computer Vision and Pattern Recognition (CVPR), Jun. 13-18, 2010, pp. 2141-2148.

P. F. Felzenszwalb et al., "Object Detection with Discriminatively Trained Part Based Models", IEEE Transactions on Pattern Analysis and Machine Intelligence, 2010, 20 pages.

S.Y. Chien et al., "Fast Video Segmentation Algorithm with Shadow Cancellation, Global Motion Compensation, and Adaptive Threshold Techniques", IEEE Transactions on Multimedia, vol. 6, No. 5, Oct. 2004, pp. 732-748.

P. Salembier, "Region-Based Representations of Image and Video: Segmentation Tools for Multimedia Services", IEEE Transactions on Circuits and Systems for Video Technology, vol. 9, No. 8, Dec. 1999, pp. 1147-1169.

I, Koprinska et al., "Temporal video segmentation: A survey", Signal Processing: Image Communication 16, 2001, pp. 477-500.

A.X. Falcao et al., "An Ultra-Fast User-Steered Image Segmentation Paradigm: Live Wire on the Fly", IEEE Transactions Medical Imaging, vol. 19, No. 1, Jan. 2000, pp. 55-62.

T. Seeman et al., "Digital Image Processing using Local Segmentation", School of Computer Science and Software Engineering Faculty of Information Technology, Monash University, Australia, Submission for degree of Doctor of Philosophy, Apr. 2002, 287 pages.

Avidan, Shai, and Ariel Shamir. "Seam carving for content-aware image resizing." ACM Transactions on graphics (TOG). vol. 26, No. 3. (2007).†

Gould, Stephen, Richard Fulton, and Daphne Koller. "Decomposing a scene into geometric and semantically consistent regions." IEEE 12th international conference on computer vision (2009).†

Kato, Zoltan, and Ting-Chuen Pong. "A Markov random field image segmentation model for color textured images." Image and Vision Computing 24.10 (2006): 1103-1114.†

* cited by examiner
† cited by third party

VISION ENHANCEMENT APPARATUS FOR A VISION IMPAIRED USER

CROSS-REFERENCE TO RELATED APPLICATIONS

The present application claims priority from Australian Provisional Patent Application No 2013902718 filed on 22 Jul. 2013, the content of which is incorporated herein by reference.

TECHNICAL FIELD

This disclosure concerns enhancing vision. In particular, but not limited to the disclosure concerns a method, software and a computer system for enhancing vision.

BACKGROUND ART

Following the enormous success achieved by bionic ears in returning hearing to profoundly deaf people, interest has now turned to developing a bionic eye that will return sight to the blind.

The eye operates by focussing tight onto the retina which in turn passes signals to the brain, via the optic nerve, where they are processed to provide sight. Partial or total blindness can be caused by damage or malfunction of any of the elements in the chain from eye to brain. However, many common forms of blindness results from damage to the retina, for instance macular degeneration leads to deterioration in the cells of the fovea, causing a blind spot in the centre of the field of vision; but leaving the peripheral vision intact. The idea behind the bionic eye is to artificially stimulate the retina using an electrode array implanted on top of it. Other visual aids, such as vision spectacles stimulate the retina using light but control the images presented before the user.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

DISCLOSURE OF INVENTION

A computer implemented method for enhancing vision for a vision impaired user comprises:
  determining based on input image data a shape associated with an object represented by the input image data;
  determining for each of multiple areas of the input image data a coverage value that indicates to what extent the shape covers that area of the input image, each of the multiple areas being associated with one of multiple imaging elements of a vision enhancement apparatus; and
  determining an output value for each of the multiple imaging elements of the vision enhancement apparatus, such that when the output values are applied to the imaging elements to create a visual stimulus, a contrast is perceivable between a first element and a second element based on their respective coverage values.

It is an advantage that a contrast is perceivable between pixels based on coverage values. As a result, an object that would disappear using conventional downsampling methods can be preserved.

Determining the output value may be such that a contrast is perceivable between a first element having a coverage value above a first coverage threshold and a second element having a coverage value below a second coverage threshold.

The first coverage threshold may be substantially the same as the second coverage threshold.

Determining the shape may comprise determining an object class for the object and the shape is a shape of the determined object class.

It is an advantage that an object class is determined. Since multiple objects of the same class occur multiple times, the shape of the actual object can be abstracted by the object class and the shape of the object itself does not need to be determined individually each time an object of the same object class is present.

It is a further advantage that the shape is the shape of the determined object class because the shapes of object classes are known and are therefore more accurate than a shape that is determined 'on the fly'.

Determining the object class may comprise selecting one or more of multiple object classes.

Selecting one or more of multiple object classes may be bases on a trained classifier.

It is an advantage that a trained classifier provides a robust and computationally efficient way of selecting the one or more object classes.

Each of the multiple object classes may be labelled as either critical or non-critical and the method may comprise
  if the determined object class is non-critical, downsampling the shape to the multiple imaging elements; and
  if the determined object class is critical, performing the steps of determining the coverage and determining the output value.

It is an advantage that critical objects, such as lamp posts are preserved while non-critical objects are downsampled which is computationally less complex.

Each of the multiple object classes may be labelled as either critical or non-critical based on a size of the object or the object class or both.

The coverage threshold may be based on the object class.

It is an advantage that different object classes may have different coverage thresholds. As a result, more important object classes can take priority over less important object classes.

Determining the output value may comprise:
  determining whether the contrast between the first element and the second element is perceivable; and
  responsive to determining that the contrast is not perceivable modifying the input image data to make the contrast perceivable.

The area associated with the first element and the area associated with the second element may be on opposed sides of a boundary of the object.

The multiple imaging elements may be located along a boundary of an object.

The method may further comprise repeating the steps of the method for multiple images of a video such that sub-pixel information becomes perceivable when the object moves between areas associated with different imaging elements.

Determining the shape associated with the object may comprise determining multiple super-pixels based on the input image data such that the multiple super pixels together represent the shape associated with the object.

The method may further comprise repeating the steps of the method for multiple frames of a video as input image data, wherein the shape associated with the object of a later frame may be based on the shape associated with the same object of an earlier frame, such that when the output values are applied to the imaging elements, it is perceivable that the shape of the earlier frame is associated with the same object as the shape of the later frame.

As an advantage the method allows a user to perceive the same object across multiple frames even where the object moves across the field of vision of the camera. As a result, the segmentation is stable over time, which means that the shape does not jump between representing different objects.

The output value may be based on multiple intensity values that are distinguishable by the vision impaired user.

The imaging elements may be stimulation electrodes and the output value may be a stimulation intensity.

The method may further comprise determining based on the input image data an object class for each point of the input image data such that the object classes minimise a cost function, the cost function may be based on a graph that provides first edges between points of the image being within a predetermined spatial distance and second edges between points the image being within a predetermined temporal distance.

The graph may comprise one or more fully connected subgraphs with size larger than two.

Software, when installed on a computer, causes the computer to perform the above method.

A computer system for enhancing vision for a vision impaired user comprises:

an input port to receive input image data;

a processor
- to determine based on input image data a shape associated with an object represented by the input image data,
- to determine for each of multiple areas of the input image data a coverage value that indicates to what extent the shape covers that area of the input image, each of the multiple areas being associated with one of multiple imaging elements of a vision enhancement apparatus, and
- to determine an output value for each of the multiple imaging elements of the vision enhancement apparatus, such that when the output values are applied to the imaging elements to create a visual stimulus, a contrast is perceivable between a first element and a second element based on their respective coverage values; and an output port to provide access to the determined output values.

Optional features described of any aspect of method, software or computer system, where appropriate, similarly apply to the other aspects also described here.

BRIEF DESCRIPTION OF DRAWINGS

An example will be described with reference to

BEST MODE FOR CARRYING OUT THE INVENTION

Figure 1:
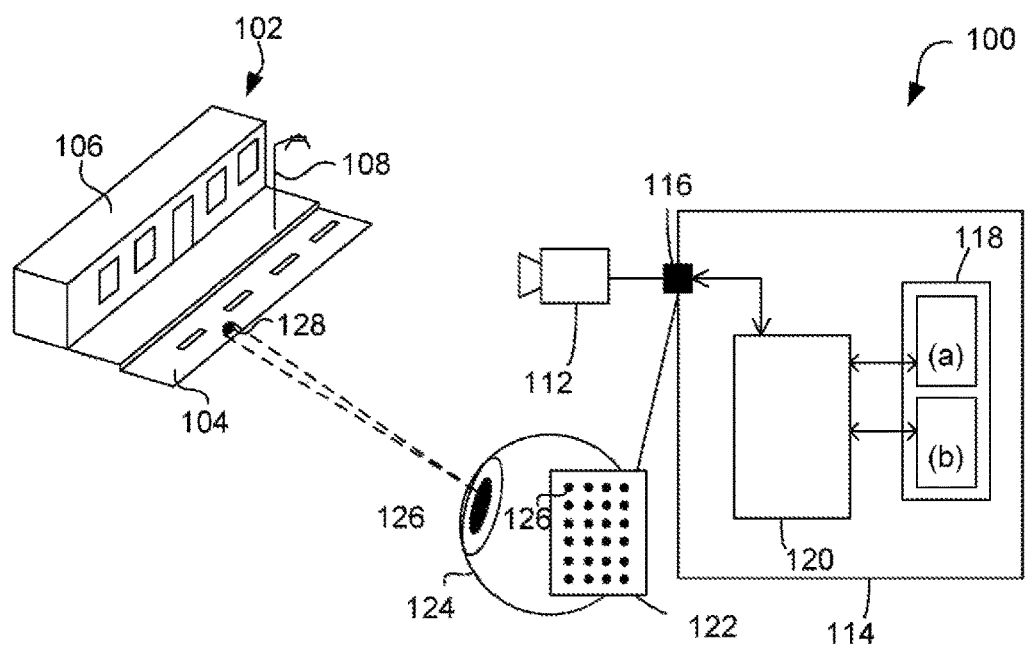
FIG. 1 illustrates a computer system 100 of a vision enhancement apparatus.

FIG. 1 illustrates a computer system 100 of a vision enhancement apparatus that enhances the vision of a scene 102. In this example, the scene 102 comprises a street 104, a house 106 and a lamp pole 108.

The computer system 100 comprises a high resolution video camera 112, such as 640×480 pixels with 8 bit per pixel, and a computer 114. The camera may be a greyscale camera or a colour camera. For simplicity of explanation 'brightness' is used herein to denote an image value in a greyscale image. However, it is noted that brightness can be replaced by luminance when an RGB image is converted to CIELAB space. Other alternatives to brightness for contrast determination may, of course, also be used.

The computer 114 comprises a data port 116, a program memory 118(a), a data memory 118(b) and a processor 120. The processor 120 receives video data from the camera 112 via data port 116, which is stored in local data memory 118(b) by processor 120. The video data represents images of a scene, such as a sequence of frames.

The processor 120 max receive data, such as image data, from data memory 118(b) as well as from the data port 116. In one example, the processor 102 receives and processes the images in real time. This means that the processor 214 performs the method of FIG. 3 every time a new image is received from the camera 112 and completes this calculation before the camera 112 send the next image, such as the next image of a video stream.

It is to be understood that any kind of data port may be used to receive data, such as a network connection, a memory interface, a pin of the chip package of processor 120, or logical, ports, such as IP sockets or parameters of functions stored on program memory 118(a) and executed by processor 120. These parameters may be stored on data memory 118(b) and may be handled by-value or by-reference, that is, as a pointer, in the source code.

The processor 120 may receive data through all these interfaces, which includes memory access of volatile memory, such as cache or RAM, or non-volatile memory, such as FLASH memory.

The data port 116 is further connected to stimulation electrode array 122 comprising 24 imaging elements, such as stimulation electrodes. Although stimulation electrodes are used here to explain the process, other imaging elements, such as pixels, may also be used. The stimulation electrodes stimulate the retina of an eye 124 of a vision impaired user. Each imaging element, such as imaging element 126, for example, has a particular field of view, that is an area of the input image. In a healthy eye light from a particular area 128 in the scene 102 is focussed by the lens of the eye onto a photoreceptor cell. The brain combines the signals from all photoreceptor cells to build a visual impression of the scene 102.

A vision enhancement apparatus replaces parts of this functionality. Camera 112 captures input image data and multiple areas in the input image data are associated with the stimulation electrodes of the electrode array 122 similar to the photoreceptor cells in the healthy eye. This association may be determined by the processor 120 or may be predetermined and stored on the data, memory 118(b) in form of pixel coordinates for each imaging element.

Typically, electrode arrays 122 are limited in their spatial resolution, such as 4×6, and in their dynamic range, that is, number of intensity values, such as 3 bit resulting in 8 different values. However, camera 112 can capture high resolution image data, such as 640×480 with 8 bit. When the dynamic range of the input image data is downsampled using existing, techniques, small differences in brightness may be lost.

Figure 2:
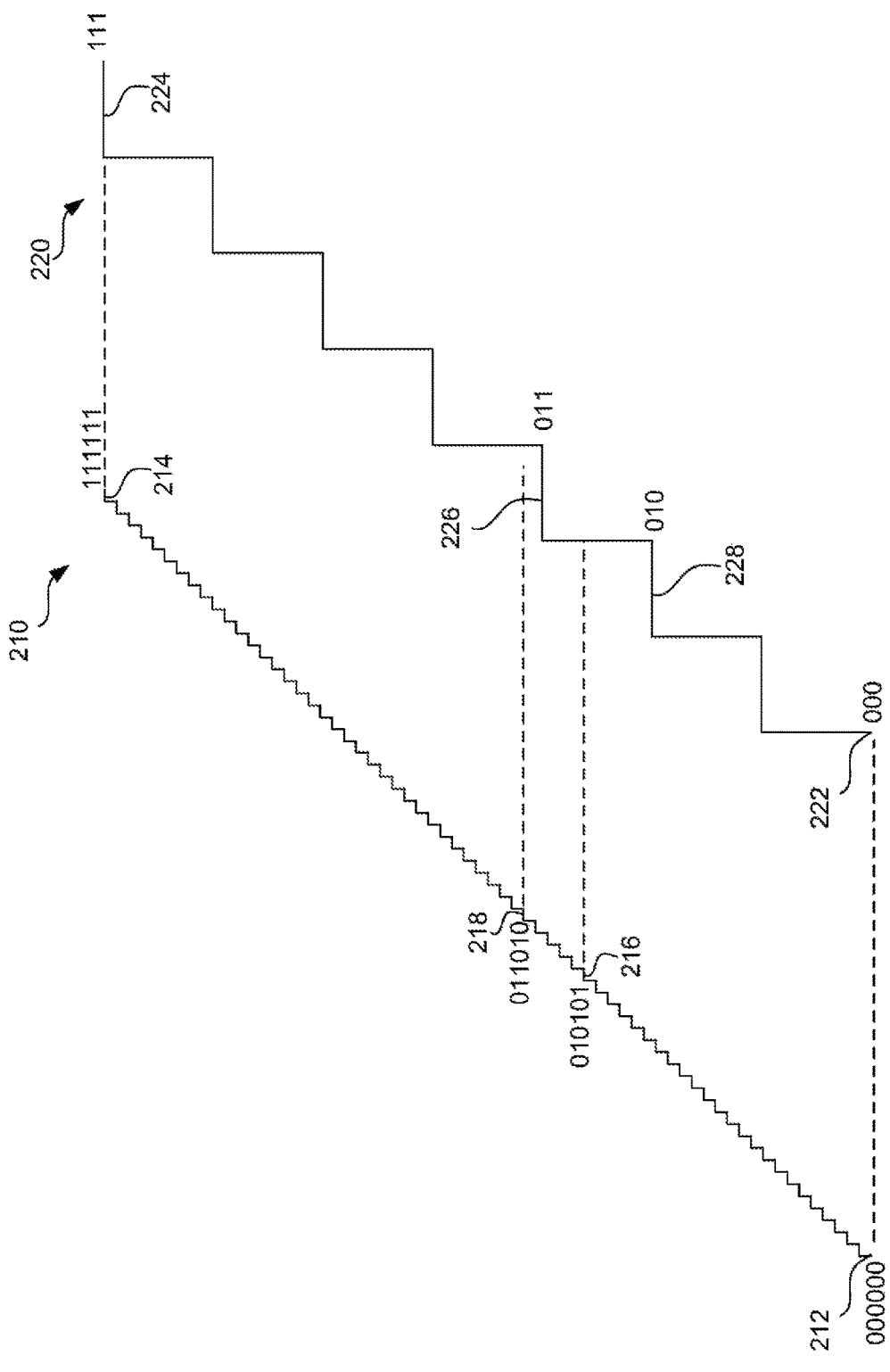
FIG. 2 illustrates the downsampling of a high dynamic range to a low dynamic range.

FIG. 2 illustrates the downsampling of a high dynamic range 210 to a low dynamic range 220. In this example, the brightness values in high dynamic range 210 are represented by six bit resulting in 64 different values between black 212 and white 214. Brightness values in the low dynamic range 220 are represented by 3 bit resulting in 8 different values between black 222 and white 224. First exemplary value 216 and second exemplary value 218 have a difference of 5 steps in the high dynamic range 210 and a difference is clearly visible.

In this example, first value 216 is the value of the input image for the street 104 and the second value 218 is for the house 106, which means the house 106 is slightly brighter than the street 104. If the image data is now downsampled to the low dynamic range 220, both values 216 and 218 are converted to the same value 226 and as a result, the vision impaired user is not able to distinguish the street 104 from the house 106, which is clearly a problem. To solve this problem, the shape of the street 104 and the house 106 is determined and it is ensured that when the output values of the low dynamic range are applied to the imaging elements 122, the user can perceive a difference between the street 104 and the house 106.

In one example, the stimulation output for each step of the low dynamic range 220 and the number of steps in the low dynamic range 220 is such that the vision impaired user can perceive a contrast between each step of the low dynamic range 220. This means that if two output values differ by one step on the low dynamic range 220, it is certain that the user can distinguish the two output values, that is, perceive a contrast between these two output values.

Figure 3:
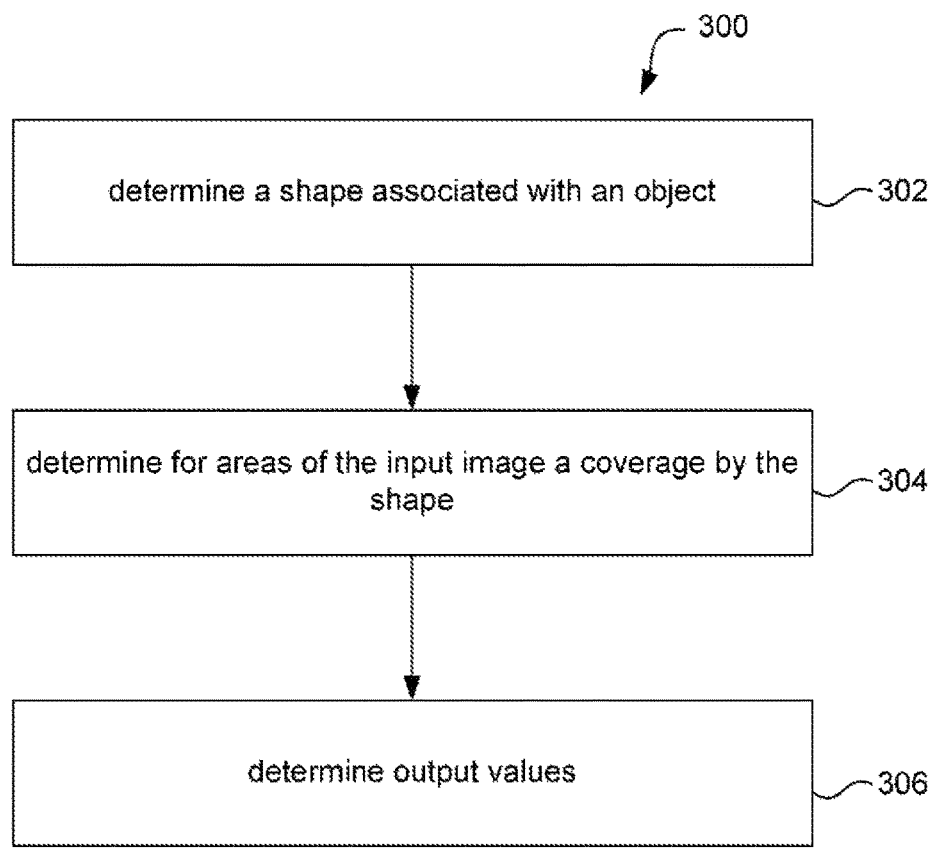
FIG. 3 illustrates a method for enhancing vision for a vision impaired user.

The processor 120 uses software stored in program memory 118(a) to perform the method shown in FIG. 3. In this sense the processor 120 performs the method of enhancing vision. The processor processes input image data and determines the shape of the street 104, the house 106 and the lamp pole 108 represented in the input data received from camera 112. The processor then determines for the areas of the electrodes a coverage by the shapes and determines an output value for the electrodes, such as a stimulation intensity represented by a stimulation voltage, number of pulses, pulse duration or simply a number value between 0 and 100 that is later interpreted by a driving circuit of the electrode array 122.

FIG. 3 illustrates a method 300 for enhancing vision for a vision impaired user as performed by processor 120. The method of FIG. 3 may be seen as a blueprint or pseudo-code of software that is compiled, stored on program memory 118(a) and executed by processor 120.

The processor 120 receives input image data from camera 112 and determines 302 based on the input image data a shape associated with an object represented by the input image data. Alternatively, the processor 120 retrieves the video data from memory 118(b), such as a video buffer, or via a computer network, such as the Internet.

In this context 'associated with an object' can mean that the shape is the shape of the object itself, such as the object of the particular house 106 or that the shape is the shape of an object class, such as a generalised car shape rather than the shape of one particular car.

Further, the determined shape may be the shape of a particular object but the processor 120 also determines the object class. For example, the shape is the exact shape of a VW Golf seen from the side and the processor 120 determines that this is a car.

In one example, multiple object classes with associated shapes are stored on data memory 118(b). Based on the input image data, the processor 120 determines an object class for an object in the image data. For example, the processor 102 determines that the thin, tall object 108 belongs to the object class 'lamp pole' and retrieves the shape for that object class from data memory 118(b). In the example explained below, the determination of the object class is an integral part of the segmentation algorithm.

The disclosed approach can be applied in offline or online streaming fashion. In the following, we consider the problem of segmenting a sequence of image frames. The sequence can be taken from the caching buffer of a camera input, or a moving window spanning from t−T+1 to t in the video stream (T frames in total).

We formulate the video segmentation as a (super-)pixel labeling problem, in which we assign each (super-)pixel in the video clique a pre-defined label. The label set can be object classes (person vs tree), their geometric properties (vertical vs horizontal), and/or the instance (car 1 vs car 2). Having multiple object classes means that the processor 120 selects one of the multiple object classes for each object in the image. The processor 120 may select more than one object class if the object belongs to multiple classes, for example, a region can be 'building' or 'wall' or 'vertical structure'. To label the video pixels, we first introduce the image representation used in our method and then define a probabilistic model for the pixel labels.

We adopt a superpixel representation of images, in which an image is partitioned into small regions with uniform appearance. However, our model can be extended to pixel representation. For each image frame, we compute the super-pixel based on the SLIC algorithm [1].

Figure 4:
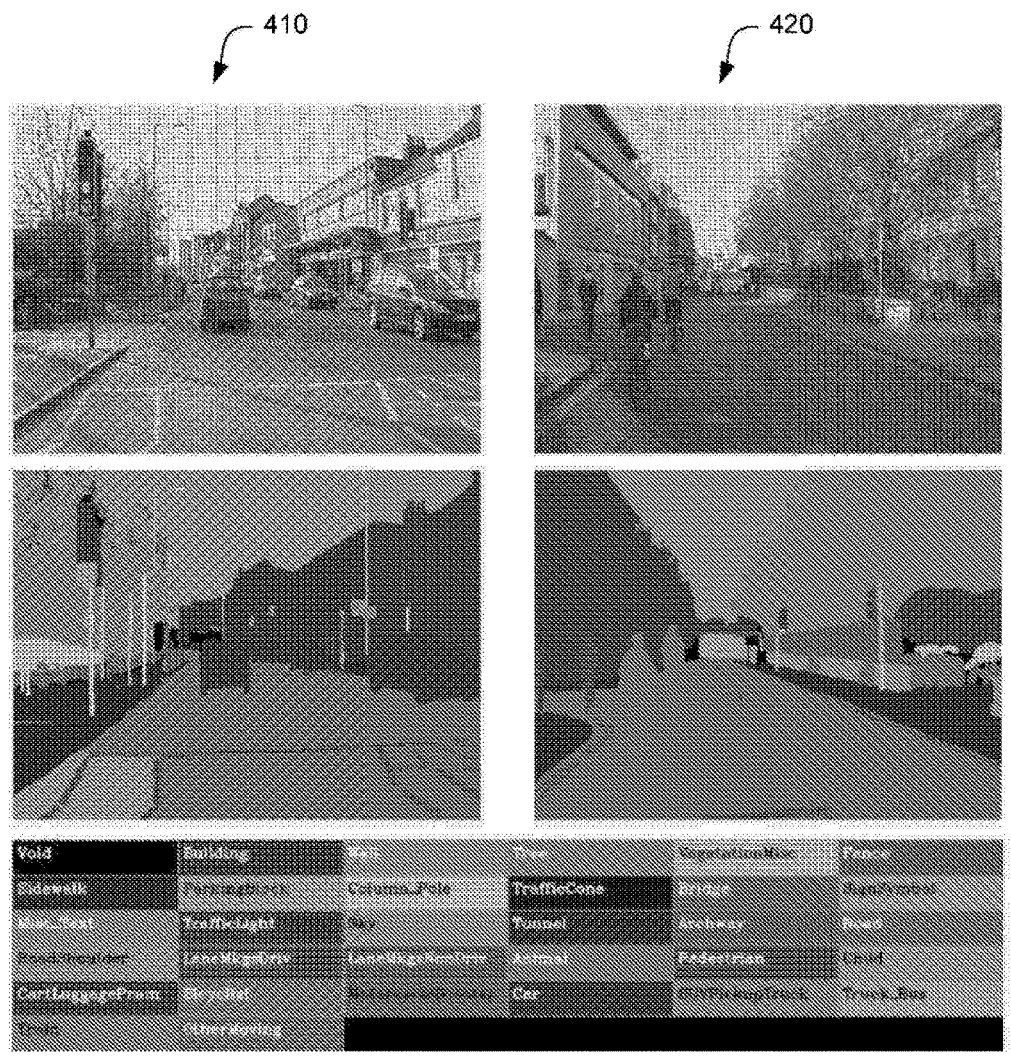
FIG. 4 illustrates two examples of a superpixelized image frame.

FIG. 4 illustrates a first example 410 and a second example 420 of superpixelized image frames from [22]. We denote the i th superpixel at t frame as $s_i^t$, and all the superpixels at time t as $S^t$. The top row shows examples of two frames with superpixel boundaries highlighted while the bottom row shows the groudtruth label of semantic classes. The data set is from [4].

In addition, we compute the optical flow for each frame based on TV-L1 flow estimation method [19]. The optical flow is computed for each pixel in TV-L1, and thus we estimate the superpixel optical flow by averaging the flow values within each superpixel region. Note that our optical flow is in backward direction of time, that is, the flow is from t frame to t−1 frame. We denote the flow vector of $s_i^t$ as $f_i^t \in R^2$, and all the flow at time t as $F^t$. We also denote the center position of superpixel $s_i^t$ on the image plane as $x_i^t$.

Given T frames, $\{I^t\}_{t=1}^T$, their superpixels, $\{S^t\}_{t=1}^T$, and the flow, $\{F^t\}_{t=2}^T$, we build a graph G=(V, E) on the image frame set. Each node of the graph corresponds to a superpixel and the graph edges connect neighboring superpixels in the following sense.

Spatial neighborhood: A superpixel $s_i^t$ is connected to every superpixel within a predefined spatial range in the frame t. One option is the superpixels adjacent to $s_j^t$, that is, they share the superpixel boundaries. Alternatively, we can introduce long-range interaction by connecting superpixels within a radius R, i.e., $\{s_j^t : \|x_j^t - x_i^t\| < R\}$.

Temporal neighborhood: A superpixel $s_i^t$ is also connected to superpixels in other frames. We first connect $s_i^t$ to the superpixels in $I_{t-1}$ and $I_{t+1}$, and within a distance radius R. That is, $\{s_j^m : \|x_j^m - x_i^t\| < R\}$, m=t-1, t+1. Optionally, we can introduce long-range temporal dependency by connecting to frames $$I_{\{t-w, \ldots, t-1, t+3, \ldots, f+w\}}.$$

In addition, we connect $s_i^t$ to the superpixels in the previous frame after considering the optical flow $f_i^t$. That is, $\{s_j^{t-1} : \|x_j^{t-1} - x_i^t - f_i^t\| < R\}$. In some examples, the method is applied to an individual image that is not a frame of a video. In that case, there is no connection to other frames and the graph comprises only the super-pixels of the single image.

The graph may contain unary and pairwise connections and there may be higher-order terms in the graph. A higher-order term means a graph clique (fully connected subgraph) with size larger than two. In other word, a graph can be sparsely or densely connected.

We build a probabilistic graphical model on the graph G. Each node in the graph $s_i^t$ is associated with a random variable $y_i^t$, which represent the semantic/object class of the superpixel $s_i^t$. Assume we have L classes, and then $y_i^t \in \{0, 1, \ldots, L\}$, where 0 is the unknown class. Our probabilistic model defines a joint distribution of all the superpixels' label variables Y in T frames, P(Y), by a set of potential functions as follows.

More specifically, we design four types of potential functions, which are defined on the nodes (unary potential $\phi_d(y_i)$, the edges connecting spatial neighbors (spatial pairwise potential $\psi_s(y_i, y_j)$), and the edges connecting temporal neighbors (temporal pairwise potential $\psi_t(y_i, y_j)$), and higher-order term $a_c(y_c)$ [21] where $y_c$ are cliques in our graph of size larger than 2. Our joint distribution P(Y) thus has the following form.

$$P(Y \mid \{I\}_{t=1}^T) = \frac{1}{Z} \exp(-E(Y)) \quad (1)$$

where the energy function E(•) consists of three terms $$E(Y) = \sum_t \sum_i \phi_d(y_i^t) + \sum_t \sum_{(i,j) \in N_s} \psi_s(y_i^t, y_j^t) + \quad (2)$$

$$\sum_{|t-u| \leq w(i,j) \in N_t} \psi_t(y_i^t, y_j^u) + + \sum_c \psi_c(y_c)$$

Here $N_s$ and $N_t$ are the spatial and temporal neighborhood respectively. The clique c can be a group of super-pixels similar in color or motion.

The data term provides bottom-up image cues to the semantic labeling of superpixels, including color, shape and position. We choose a linear function with the form, $$\phi_d(y_i^t) = -\omega^T g(s_i^t) y_i^t \quad (3)$$

where ω is the weighting parameter, $g(s_i^t)$ is an image feature vector computed from the image region around $s_i^t$. We can also compute a spatial-temporal feature vector, but the extension is straightforward. We use the following features: average color in CIE-Lab space, histogram of filter-bank output [16], dense HOG features [7], and their image positions. We train a linear classifier to predict the semantic labels and use its score function as the unary term.

The spatial smoothness term imposes the label smoothness across image plane, that is, neighboring superpixels usually share the same label. We adopt the Potts model in MRF literature, which specifies the spatial pairwise potential as $$\psi_s(y_i^t, y_j^t) = \beta(1 - aP(e_{ij}))e^{-\|x_i^t - x_j^t\|^2 / \sigma_d^2} \delta(y_i^t \neq y_j^t) \quad (4)$$

where $P(e_{ij})$ is the average boundary probability between $s_i^t$ and $s_j^t$ and $\beta, \alpha$ are weighting coefficients. In one example, these weighting coefficients are estimated from a training dataset, which may depends what unary terms are used. In another example the value of these coefficents is 0.9. $\delta(u)$ is a indicator function that takes 0 if u is false and 1 otherwise.

We can also run an object detector on the image, and use their output to identify potential support of the object instances. Within those support area, we can introduce a pairwise term based on the shape prior of the object class [12].

The temporal smoothness term takes a similar form to the spatial term. It also encourages temporal neighbors to share the same label. As in the spatial term, we weigh the energy/cost by the color similarity and the flow similarity:

$$\psi_t(y_i^t, y_j^u) = \quad (5)$$

$$\gamma e^{-\|c_i^t - c_j^u\|^2 / \sigma_c^2 - \|f_i^t - f_j^u\|^2 / \sigma_f^2 - \|x_i^t - x_j^t\|^2 / \sigma_d^2} \cdot e^{-\|t-u\|^2 / \sigma_t^2} \delta(y_i^t \neq y_j^u)$$

where $c_i^t$ is the color feature, $\sigma_c$ and $\sigma_f$ are the standard deviation of those quantities. We set $\sigma_d$ and $\sigma_t$ to pre-defined values (spatial-temporal window size). In one example, $\sigma_d = 10$, and $\sigma_t = 10$. As above, these parameters may be tuned based on a training dataset.

We can also use a tracking method to estimate the long-term trajectories in the video and impose smoothness constraint w.r.t the trajectories [5]. Note that the temporal smoothness term is the key to maintain the stability of the segmentation.

Parameter Estimation

Given a training set as in [4], we estimate the model parameters based on piece-wise learning. The data term is trained as a linear classifier while other weighting coefficients are estimated with cross-validation on the training dataset. We can also train the whole system as a structured SVM or Conditional Random Field [2].

Segmentation by Global Inference

We segment the video clip by searching the most probable label configuration $Y^*$ given input video based on our model $P(Y \mid (I)_{t=1}^T)$. Mathematically, we have the following optimization problem, $$Y^* = \arg\max_Y P(Y \mid \{I\}_{t=1}^T) = \arg\min_Y E(Y) \quad (6)$$

Note that we segment the frames jointly in which each superpixel's label depends on not only its feature in the current and previous frames but also all the spatial-temporal neighbors. In addition, the information is propagated within our graph during inference such that the segmentation is a global decision.

In some cases the exact inference in such loopy graph is difficult to compute. However, there are efficient approximate inference algorithms for solving our problem. In the following, we list two options for doing the approximate inference in a fast way.

Mean field approximation and filtering method [11]. In this method, we can use Mean field approximation to compute the most probable configuration and a fast filtering technique to implement the computation.

Loopy belief propagation [15]. In this approach, we use a max-product message passing algorithm to efficient compute the most probable configuration. The message-passing algorithm depends on the local operation only and can be parallelized.

In the streaming scenario, we can fix the label configuration from 1 to T−1 and only infer the labeling for the T frame. This is a special case of the previous joint inference and can be implemented in a similar way. In addition, the streaming model can use the dynamic graph-cut algorithm [10] to further speed up the computation.

Referring back to the method 300 of FIG. 3, as a next step, processor 120 determines 304 for multiple areas of the input image data a coverage value that indicates to what extent the determined shape covers that area of the input image. This means that the coverage value is not a binary variable that indicates whether or not an image area shows an object but instead, is a gradual variable, such as an integer that ranges from 0 to 100, to indicate to what extent the determined, shape covers that area of the input image. In one example, the coverage value has at least three possible values, such as a first value representing the shape does not cover the area at all, a second value representing the shape partly covers the area and a third value representing the shape completely covers the area.

The coverage value may be a number of pixels of the object shape that are within the area of a particular imaging element or a percentage of the area covered by the object shape. In cases where the area of each imaging element covers the same number of pixels of the input image, counting the number of pixels of the object that are equal to the pixels of the imaging element may be computationally less expensive than computing a percentage.

In one example, the input image has an input resolution of 640×480 pixels and each stimulation electrode represents an area of 35×30 pixels of the input image, that is, each stimulation electrode represents 1,050 input pixels. In that example, an object may cover half of the entire image, that is, the object spreads over 153,600 pixels. A first image area may be partly covered by the object such that 526 pixels of the 1,050 pixels show the object and the remaining 524 pixels show the background. In this example, the coverage value is the number of pixels of the first image area that are covered by the object, that is, 526 pixels. It is noted that the number of pixels that are not covered also indicate to what extent the shape covers the object and therefore, 524 pixels may also be an alternative coverage value but this alternative is not used in present examples.

A second image area may be partly covered by the object such that 524 pixels of the 1,050 pixels show the object and the remaining 526 pixels show the background, that is, the second coverage value is 526 pixels. If the threshold in this example is 525 pixels, that is, 50% of the pixels of the input image area, then the stimulation intensity of the electrode associated with the first image area should differ from the stimulation intensity of the electrode associated with the second image area by at least on step of low dynamic range 220 in FIG. 2, which means a contrast should be perceivable.

However, an object may not be perceivable because the object covers only a small number of pixels and the spatial downsampling of the input image to the coarse spatial resolution of the electrode array 122 would result in a loss of that fine detail. For example, lamp pole 108 may cover only 5 pixels in the image data from camera 112 and the spatial downsampling simply loses this detail. However, the lamp pole 108 still covers the area of an imaging element by more than a coverage threshold, such as 5%.

To prevent the disappearing of objects the next step of method is to determine 306 an output value, that is, a stimulation value, such that a contrast is perceivable between an area with the object and an area without the object, that is, the contrast between two imaging elements is perceivable based on the coverage value of the areas. For example, the coverage value of to first element is 6% and the coverage value of a second element is 3% with a coverage threshold of 5%. The method ensures that the output value of the first area and the output value of the second area differ by at least one step of the low dynamic range.

In another example, the threshold may be different for each element such that there is a perceivable contrast if the coverage value of a first element is 45% with a first threshold of 44% and the coverage value of a neighbouring element is only 35% with a second threshold of 34%.

In yet another example, the output values may be determined such that a contrast is perceivable when a difference between the coverage value $c_1$ of a first element and the coverage value $c_2$ of a second element is above a threshold T: $|c_1-c_2| \geq T$.

Different users may have different levels of contrast that they can perceive and therefore, the step of determining the output values may depend on the particular diagnosis of the user, such that the contrast is perceivable for that user. This means the method 300 and in particular the low dynamic range 220 may be adjusted to suit a particular user, such as by adjusting the individual stimulation levels for each output value.

As a result, the method ensures that the difference in output value between the area with the lamp pole and the areas without the lamp pole is perceivable, such as by ensuring a minimum difference m output value of one step of the dynamic range.

Similarly, as mentioned earlier with reference to FIG. 2, in cases where the object and the background have a similar image values, such as brightness or colour, the object may not be perceivable as both the object image value and the background image value are mapped to the same value in the low dynamic range. This loss of contrast can be prevented by pre-processing the image data from the camera 112. This pre-processing is performed by processor 120 by determining a contrast value, such as number of quantisation steps in brightness value, between the area that covers the object and the area that does not cover the object.

The processor 120 can then determine whether the contrast is not perceivable, that is, that a trapping to the low dynamic range would result in a contrast in the output below a perceptual threshold, such as a mapping to the same value. In that case, the processor 120 increases the contrast in the input image between the object image value and the non-object image value until the contrast in the output values is perceivable. This way, the user can perceive objects that would otherwise not be perceivable.

For example, the output of the segmentation algorithm above is a set of super-pixels that are associated or labelled, with a particular object or object class, such as 'lamp pole'. The processor 120 can then access the high definition image data including the brightness values of these super-pixels and compare these brightness values to the brightness values of the surrounding super-pixels that are not labelled 'lamp pole'. This way, the processor 120 determines the contrast between the object and super-pixels that do not constitute the object. If this contrast would be not perceivable when the image is downsampled, the processor 120 increases the contrast, such as by increasing the brightness of the object if the object is already slightly brighter than the background.

This step, including increasing the contrast, may be performed along the boundary of the shape, such that the two exemplary areas are on opposite sides of the boundary. This means that for contrast determination the processor 120 does not consider the entire set of super-pixels that are labelled with a particular object or object class, but only the super pixels along and within the boundary of the object. Vice versa, instead of all the background super-pixels, only the super-pixels along and outside the boundary of the object are considered.

If any of the visual field corresponding to the output pixels near the boundary of the object (or the mean of them, or the max of the mean, or any other such function over their size), were covered by k % object, or by k % of background (where k is a constant less than 50%), then increase the contrast between the object and the boundary such that it would be sufficient to make the difference along the boundary noticeable. That is an output pixel with k % object would be noticeably different (brighter or less bright) than an output pixel nearby with no object in it. Likewise for k % background.

The processor 120 then downsamples the input image data to the output values using a method that preserves subpixel effects, such as a reconstruction filter, such as local averaging, Gaussian, or Lanczos2 or Lanczos3. Note that k % here can be defined in the absolute area of the input visual field, or could be defined as a percentage of the output value of a filter convolved with that area, say a Gaussian, or Lanczos2, whereby each input pixel value could contribute in a variable way in accordance with its position in the input visual field.

Note also that the contrast across an object or the background may vary, and this may be an adjustment of contrast such that if the area of input pixels is bigger than some threshold, or some threshold of the input size, or percentage of the output of the filter size as above, then processor 120 may adjust locally, or adjust the contrast of the whole figure such that this area is clearly contrasted. The adjustment may be a full optimization as explained in PCT/AU2013/000465, which is incorporated herein by reference, and in "On Just Noticeable Difference for Bionic Eye" (Yi Li, McCarthy, C., Barnes, N. Engineering in Medicine and Biology Society (EMBC), 2012 Annual International Conference of the IEEE).

The explanation above relates to a two-class scenario, in which processor 120 enhances the contrast between foreground object and background. The method presented above generates a stable multi-class (multiple object categories) segmentation and using the multi-class output, the processor 120 can achieve more.

In particular, processor 120 can use semantic class information to selectively enhance certain aspects of the scene. One interesting example is the layout or structure of the scene, which can be used in orientation and navigation facilitation. For instance, in an indoor setting, if the labelling of floor and wall is determined, processor 120 can enhance the boundary between them, so that the viewer can perceive the outline of the hallway floor, etc. In an outdoor setting, processor 120 can enhance certain important object classes, such as sign poles, boundaries between road and pavement, so that the viewer can plan their movement in a more informative way. Note that pure image enhancement is unstable due to dynamic scenes.

For these types of enhancement, the stable multi-class segmentation becomes important as the enhancement depends on the class information and precise boundaries between classes. The enhancement itself can be the same as the two-class setting.

The enhancement can be controlled by different values for the coverage threshold for different object classes. For example, light poles are critical and therefore, the critical object class of light poles has a lower coverage threshold, such as 2% while less important or non-critical object classes have a higher coverage threshold, such as 50%. Since small, such as narrow, objects are more likely to be lost by spatial downsampling, the coverage threshold for object classes that are known to be narrow, such as light poles, may be set to a lower value than object classes of large objects.

In another example, for non-critical objects, the image data is simply downsampled to the low spatial resolution and low dynamic range since losing this object would not be significant. However, for critical objects, processor 120 ensures that the object is perceivable as described herein. Since larger objects are less likely to disappear when downsampling the image data the object class for large objects may be set to non-critical. On the other hand, small or thin objects, such as lamp poles, may be considered critical since there is a risk that these objects disappear.

The lamp pole 108 may be critical for orientation and mobility as a potential landmark and also a potential collision hazard. The criticality may defined based on whether the object is hard to find in terms of segmentation (thin) and/or important to the user.

Figure 5A:
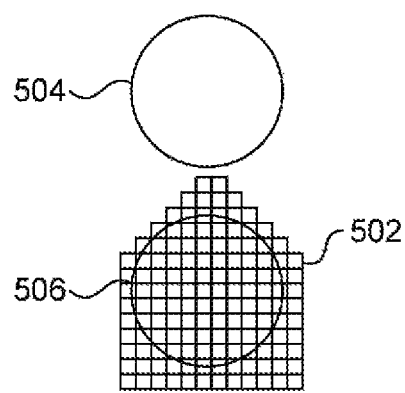
FIGS. 5a and 5b schematically illustrate different coverage of multiple areas by an object.
Figure 5B:
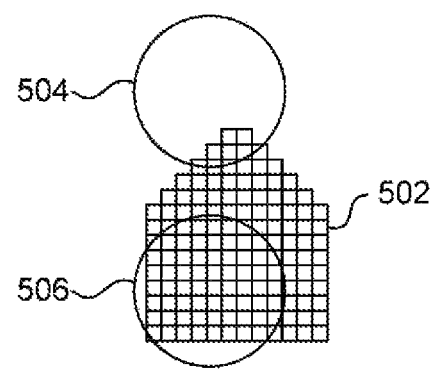

FIGS. 5a and 5b schematically illustrate different coverage of multiple areas by an object 502, such as a house, in consecutive frames of a video stream. In FIG. 5a, a first area 504 and a second area 506 is shown. The first and second areas 504 and 506 are associated with first and second stimulation electrodes, respectively, as explained above. As can be seen in FIGS. 5a and 5b, object 502 is represented by multiple super-pixels and each super-pixel comprises one or more pixels of the input image. Although the super-pixels are shown as regular squares, it is noted that in many applications, the shape of the super-pixels will be irregular.

In FIG. 5a the object 502 covers the second area 506 not to an extent but object 502 completely covers the second area 506. As a result, the output value $f_1$ of the first area 504 is the foreground value x, such as 111. On the other hand, object 502 does not cover the second area 504 at all. As a result, the output value $f_2$ of the second area is the background value n, such as 000. As mentioned earlier, the output values may be converted to stimulation pulses with stimulation intensities between zero stimulation for 000 and maximum stimulation for 111.

In FIG. 5b, the object from FIG. 5a has moved. Now, the coverage of the second area 506 is not complete but instead, object 502 covers the second area 506 to an extent and processor 102 can determine a coverage value that indicates to what extent the shape covers that area of the input image. In this example, the result for the coverage value is less than 100% by more than a coverage threshold k. As a result, the pixel value $f_2$ of the second area 506 is reduced by at least a noticeable difference $\Delta$, that is, $f_2 \leq n-\Delta$. Vice versa, the coverage value of the first area 504 is above a coverage threshold k and as a result, the pixel value $f_1$ of the first area 504 is at least a noticeable difference $\Delta$ above the background value, that is $f_1 \geq x+\Delta$. In one example, the coverage threshold is 5% and the noticeable difference $\Delta$ is the difference of one step of the low dynamic range as explained with reference to FIG. 2.

A vision impaired user can now perceive the motion of the object 502 from the location in the earlier frame in FIG. 5a to the location in the later frame in FIG. 5b by a transition of the output values of the areas 504 and 506. As a result, more information is perceivable than if the two areas were regarded separately. This is referred to as sub-pixel information and the method described above ensures that the sub-pixel information, such as the movement of an object from one stimulation electrode to a neighbouring stimulation electrode is perceivable by the vision impaired user.

The sub-pixel information is more perceivable when the segmentation of the object remains stable as described earlier with reference to Equation (5). When determining the shape, the shape associated with the object of a later frame (FIG. 5b) is based on the shape associated with the same object of an earlier frame (FIG. 5a). This means that when Equation (5) is evaluated for later frame t=1, it includes values from earlier frame t=0. As a result, when the output values are applied to the electrode array 122, it is perceivable that the shape of the earlier frame is associated with the same object as the shape of the later frame.

In one example, the output image is displayed on a computer screen for evaluating the quality of the resulting image. In this example, the output image is of a common computer image file format such as the tiff format. In a different example, the output image is converted by a process commonly referred to as phosphenisation into a format that is suitable for stimulation by a vision enhancement apparatus, such as low resolution retinal prosthesis 122 which is implanted into an eye 124 of a user.

In one example, the method uses the simulated phosphene vision system where phosphenes are built as discrete Gaussian kernels using impulse sampling of the segmented region at the phosphene location, without prior filtering. Other common methods for rendering phosphenes are to filter the image prior to sampling or after, or apply a mean or Gaussian filter over an area centred at the phosphene location. The method 300 applies phosphene rendering to both the original intensity image (for comparison) and the segmented region, that is the shape of an object in the scene determined by processor 120.

The simulated phosphene display consists of a 35×30 rectangular grid scaled to image size. Each phosphene has a circular Gaussian profile whose centre value and standard deviation is modulated by brightness at that point. In addition, phosphenes sum their values when they overlap. In one example, phosphene rendering is performed at 8 bits of dynamic range per phosphene, which is an idealised representation. In a different example, it is assumed that maximum neuronal discrimination of electrical stimulation is closer to a 3 bit rendering. In another example, there are different numbers of bits of representation at each phosphene, and this may change over time.

In one example, the vision enhancement apparatus measures an eye gaze direction and the processor 120 selects one of multiple objects of the image based on the eye gaze direction. This way, the user can select an objects for display by 'looking' at the object. For clarity purposes, in this specification stimulation of nerves by the retinal prosthesis such that a user perceives the output image is referred to as display of the output image although the optical system of the eye is bypassed.

In one example, the output image is created based on the characteristics of the vision impaired user. Most users suffering from macular degeneration have reduced vision in the centre of the field of vision while peripheral vision is effected to a lesser degree. In order to use the peripheral vision, the object is displayed in the output image off the centre and in the peripheral area of the field of vision. Other User specific adaptations may also be made, such as user-specific spatial resolution, dynamic range, minimal image value and maximal image value.

Available methods for object detections may be used. The object detection results in a bounding box, that is a boundary for sub-image 212, for each detected object and an object is selected if the determined location 214 lies within the boundary box for that object.

In one example, the vision enhancement apparatus comprises a further input device such that the user can change this setting based on the user's environment and requirements.

It will be appreciated by persons skilled in the art that numerous variations and/or modifications may be made to the specific embodiments without departing from the scope as defined in the claims.

It should be understood that the techniques of the present disclosure might be implemented using a variety of technologies. For example, the methods described herein may be implemented by a series of computer executable instructions residing on a suitable computer readable medium. Suitable computer readable media may include volatile (e.g. RAM) and/or non-volatile (e.g. ROM, disk) memory, carrier waves and transmission media. Exemplary carrier waves may take the form of electrical, electromagnetic or optical signals conveying digital data steams along a local network or a publically accessible network such as the internet.

It should also be understood that, unless specifically stated otherwise as apparent from the following discussion, it is appreciated that throughout the description, discussions utilizing terms such as "estimating" or "processing" or "computing" or "calculating", "optimizing" or "determining" or "displaying" or "maximising" or the like, refer to the action and processes of a computer system, or similar electronic computing device, that processes and transforms data represented as physical (electronic) quantities within the computer system's registers and memories into other data similarly represented as physical quantities within the computer system memories or registers or other such information storage, transmission or display devices.

The present embodiments are, therefore, to be considered in all respects as illustrative and not restrictive.

REFERENCES

[1] Achanta, R. and Shaji, A. and Smith, K. and Lucchi, A. and Fua, P. and Süsstrunk, S. Slic superpixels. *École Polytechnique Fédéral de Lausssanne (EPFL), Tech. Rep,* 2010.

[2] Blake, Andrew and Kohli, Pushmeet and Rother, Carsten. *Markov random fields or vision and image processing*. Mit Pr, 2011.

[3] G S Brindley and W S Lewin. The sensations produced by electrical stimulation of the visual cortex, *Journal of Physiology,* 196(2):479-493, 1968.

[4] Gabriel J. Brostow and Jamie Shotton and Julien Fauqueur and Roberto Cipolla. Segmentation and Recognition Using Structure from Motion Point Clouds, *ECCV* (1), pages 44-57, 2008.

[5] Brox, Thomas and Malik, Jitendra. Object segmentation by long term analysis of point trajectories, *Computer Vision—ECCV* 2010, pages 282-295. Springer, 2010.

[6] S C Chen and L E Hallum and N H Lovell and G J Suaning. Visual Acuity Measurement of Prosthetic Vision: A Virtual-Reality Simulation Study. *Neural Engineering*, 2(1):S134-45, 2005.

[7] N Dalal and B Triggs. Histograms of oriented gradients for human detection. *IEEE Conf. on Computer Vision and Pattern Recognition*, pages 886-893, San Diego, Calif., USA, 2005.

[8] M S Humayun and J D Dorn and L Da Cruz and G Dagnelie and J-A Sachet and P E Stranga and A V Cideciyan and J L Duncan and D Eliott and E Filley and A C Ho and A Santos and A B Safran and A Arditi and L V Del Priore, and R J Greenberg for the Argus II Study Group. Interim Results from the international trial of second sight's visual prosthesis. *Ophthalmology*, 119(4): 779-88, 2012.

[9] M S Humayun and J Weiland and G Y Fujii and R Greenberg and R Williamson and J Little and B Mech and V Cimmarusti and G Van Boemel and G Dagnelie and E deJuan Jr. Visual perception in a blind subject with a chronic microelectronic retinal prosthesis. *Vision Research*, 43:2573-2585, 2003.

[10] Kohli, Pushmeet and Torr, Philip H S. Dynamic graph cuts for efficient inference in markov random fields. *Pattern Analysis and Machine Intelligence, IEEE Transactions on*, 29(12):2079-2088, 2007.

[11] Krähenbühl, Philipp and Koltun, Vladlen. Efficient inference in fully connected CRFs with Gaussian edge potentials. *arXiv preprint arXiv:* 1210.5644, 2012.

[12] Kumar, M Pawan and Ton, P H S and Zisserman, Andrew. Obj cut. *Computer Vision and Pattern Recognition, 2005. CVPR 2005. IEEE Computer Society Conference on*, pages 18-25, 2005. IEEE.

[13] P Lieby and N Barnes and J G Walker and A Scott and L Ayton. Evaluating Lanczos2 Image Filtering for Visual Acuity In Simulated Prosthetic Vision. *ARVO*, 2013.

[14] D Nanduri and M Humayun and R Greenberg and M J McMahon and J Weiland. Retinal Prosthesis Shape Analysis. *IEEE Int. Conf. of Engineering in Medicine and Biology Society (EMBC)*, pages 1785-8, 2008.

[15] Schwing, Alexander and Hazan, Tamir and Pollefeys, Marc and Urtasun, Raquel. Distributed message passing for large scale graphical models. *Computer Vision and Pattern Recognition (CVPR), 2011 IEEE Conference on*, pages 1833-1840, 2011. IEEE.

[16] Shotton, Jamie and Winn, John and Rother, Carsten and Criminisi, Antonio. Textonboost: Joint appearance, shape and context modeling for multi-class object recognition and segmentation. *Computer Vision—ECCV* 2006, pages 1-15. Springer, 2006.

[17] R Wilke and V-P Gabel and H Sachs and K-U Bartz-Scmidt and F Gekeler and D Besch and P Szurman and A Stett and B Wilhelm and T Peters and A Harscher and U Greppmaier and S Kibbel and H Benav and A Bruckmarin and K Stingl and A Kusnyerik and E Zrenner. Spatial resolution and perception of patterns mediated by a subretinal 16-Electrode array in patients blinded by hereditary retinal distrophyies. *Investigative Ophthalmology and Visual Science*, 52(8):5995-6003, 2011.

[18] D R Williams and H Hofer, *The Visual Neurosciences: Volume* 1, chapter Formation and Acquisition of the Retinal Image, pages 795-810. MIT Press, Cambridge Mass., 2004.

[19] Zach, Christopher and Pock, Thomas and Bischof, Horst. A duality based approach for realtime TV-L 1 optical flow. *Pattern Recognition:*214-223, 2007.

[20] E Zrenner and K U Bartz-Schmidt and H Benav and D Besch and A Bruckmann and V-P Gabel and F Gekeler and U Greppaier and A Harscher and S Kibbel and J Kock and A Kusnyerik and T Peters and K Stingl and A Stett and P Szurman and B Wilhelm and R Wilke. Subretinal electronic chips allow blind patients to read letters and combine them to words. *Proc. Royal Society of London B: Biological Sciences*, 278:1489-1497, 2011.

[21] Kohli, P., Ladický, L., & Torr, P. H. S. (2009). Robust Higher Order Potentials for Enforcing Label Consistency. International Journal of Computer Vision, 82(3), 302-324. doi: 10.1007/s11263-008-0202-0.

[22] Brostow, G. J., Fauqueur, J., & Cipolla, R. (2009). Semantic object classes in video: A high-definition ground truth database. Pattern Recognition Letters, 30(2), 88-97, doi:10.1016/j.patrec.2008.04.005.

The invention claimed is:

1. A computer implemented method for enhancing vision for a vision impaired user, the method comprising: receiving input image data comprising multiple areas, each of the multiple areas of the input image data associated with one of multiple stimulation electrodes of a vision enhancement apparatus; determining, based on the input image data, a shape associated with an object represented by the input image data; determining, for each of multiple areas of the input image data, a coverage value that indicates to what extent the shape covers that area of the input image, determining stimulation intensity for each of the multiple stimulation electrodes of the vision enhancement apparatus, such that when the output values stimulation intensities are applied to the imaging elements to create a visual stimulus, a contrast is perceivable between a first element and a second element based on their respective coverage values; and applying the stimulation intensity to the stimulation electrodes.

2. The method of claim 1, wherein determining the stimulation intensity is such that a contrast is perceivable between a first element having a coverage value above a first coverage threshold and a second element having a coverage value below a second coverage threshold.

3. The method of claim 1, wherein determining the shape comprises determining an object class for the object and the shape is a shape of the determined object class.

4. The method of claim 3, wherein determining the object class comprises selecting one or more of multiple object classes.

5. The method of claim 4, wherein selecting one or more of multiple object classes is based on a trained classifier.

6. The method of claim 4, wherein each of the multiple object classes is labelled as either critical or non-critical and the method comprises:
  if the determined object class is non-critical, downsampling the shape to the multiple imaging elements; and
  if the determined object class is critical, performing the steps of determining the coverage and determining the stimulation intensity.

7. The method of claim 4, wherein each of the multiple object classes is labelled as either critical or non-critical based on a size of the object or the object class or both.

8. The method of claim 4, wherein the coverage threshold is based on the object class.

9. The method of claim 1, wherein determining the stimulation intensity comprises:
determining whether the contrast between the first element and the second element is perceivable; and
responsive to determining that the contrast is not perceivable modifying the input image data to make the contrast perceivable.

10. The method of claim 9, wherein the area associated with the first element and the area associated with the second element are on opposed sides of a boundary of the object.

11. The method of claim 1, wherein the multiple imaging elements are located along a boundary of an object.

12. The method of claim 1, further comprising repeating the steps of the method for multiple images of a video such that sub-pixel information becomes perceivable when the object moves between areas associated with different imaging elements.

13. The method of claim 1, wherein determining the shape associated with the object comprises determining multiple super-pixels based on the input image data such that the multiple super-pixels together represent the shape associated with the object.

14. The method of claim 1, further comprising repeating the steps of the method for multiple frames of a video as input image data, wherein the shape associated with the object of a later frame is based on the shape associated with the same object of an earlier frame, such that when the stimulation intensities are applied to the imaging elements, it is perceivable that the shape of the earlier frame is associated with the same object as the shape of the later frame.

15. The method of claim 1, wherein the stimulation intensity is based on multiple intensity values that are distinguishable by the vision impaired user.

16. The method of claim 1, further comprising determining based on the input image data an object class for each point of the input image data such that the object classes minimises a cost function, the cost function being based on a graph that provides:
first edges between points of the image being within a predetermined spatial distance; and
second edges between points of the image being within a predetermined temporal distance.

17. The method of claim 16, wherein the graph comprises one or more fully connected subgraphs with size larger than two.

18. A non-transitory computer-readable medium with computer-executable instructions stored thereon, that when executed by a computer causes the computer to perform the method of claim 1.

19. A computer system for enhancing vision for a vision impaired user, the computer system comprising:
an input port to receive input image data comprising multiple areas, each of the multiple areas of the input image data being associated with one of multiple stimulation electrodes of a vision enhancement apparatus;
a processor to determine, based on the input image data, a shape associated with an object represented by the input image data;
to determine, for each of the multiple areas of the input image data, a coverage value that indicates to what extent the shape covers that area of the input image,
to determine stimulation intensity for each of the multiple stimulation electrodes of the vision enhancement apparatus, such that when the stimulation intensities are applied to the imaging elements to create a visual stimulus, a contrast is perceivable between a first element and a second element based on their respective coverage values, and
to apply the stimulation intensities to the stimulation electrodes.

* * * * *